United States Patent
Jones et al.

(10) Patent No.: US 6,888,008 B2
(45) Date of Patent: May 3, 2005

(54) PROCESS FOR PREPARING 3-ISOCHROMANONE

(75) Inventors: Raymond Vincent Heavon Jones, Grangemouth (GB); Alan John Whitton, Grangemouth (GB); Jennifer Ann White, Grangemouth (GB); David John Ritchie, Grangemouth (GB); Robin Fieldhouse, Grangemouth (GB); Kirstin Maccormick, Grangemouth (GB); Logan Thomson Nisbet, Grangemouth (GB); Paul Richard Evans, Grangemouth (GB); Colin John Bennie, Grangemouth (GB)

(73) Assignee: Syngenta Limited (GB)

( * ) Notice: Subject to any disclaimer, the term of this patent is extended or adjusted under 35 U.S.C. 154(b) by 310 days.

(21) Appl. No.: 09/810,458

(22) Filed: Mar. 16, 2001

(65) Prior Publication Data

US 2002/0143193 A1 Oct. 3, 2002

(51) Int. Cl.[7] ............................................. C07D 311/74
(52) U.S. Cl. ..................................................... 549/290
(58) Field of Search .......................................... 549/290

(56) References Cited

U.S. PATENT DOCUMENTS

| 4,424,394 A | 1/1984 | Schneider |
| 4,713,484 A | 12/1987 | Epstein |
| 5,886,211 A | * 3/1999 | Hirai et al. |

FOREIGN PATENT DOCUMENTS

| DE | A-2410782 | 3/1974 |
| DE | A-2526046 | 6/1974 |
| EP | 0 834 497 A | 4/1998 |
| GB | WO 99/103365 | * 3/1999 |
| WO | WO 98 56784 A | 12/1998 |
| WO | WO 99 10335 A | 3/1999 |

OTHER PUBLICATIONS

J. Org. Chem. (1993) 58, 1538–45.
J. Kiji et al., Chem. Lett. 957–960, 548.
L. Cassar et al., J. Organometallic Chem., 121 (1976) C55–56.
X. Huang et al., Chem. & Ind., Sep. 3, 1990, 548.
V, Grushin et al., Organometallics, 12 (5), 1890–1901 (1993).
T. Ito et al., Bull. Chem. Soc. Japan, 48 (7), 2091–2094 (1975).
D. Bergbreiter et al., J. Mol. Catalysis, 74 (1992) 406–419.
C.W. Kohlpaintner et al., J. Molecular Catalysis A: Chemical, 116 (1997), 259–267.
A. Cowell and J.K. Stille, J. Am. Chem. Soc., 102:12 (Jun. 4, 1980) 4193–4198.
S.C Shim et al., Bull. Korean Chem. Soc., vol. 9, No. 3 (1988), 185–187.
Z. Shanyan et al., J. Molecular Catalysis, vol. 1, No. 2 (1987) 115–119.

* cited by examiner

Primary Examiner—Paul A. Zucker
(74) Attorney, Agent, or Firm—Rose M. Allen

(57) ABSTRACT

A process for the preparation of 3-isochromanone which comprises contacting an o-xylene-$\alpha,\alpha'$-dihalide with carbon monoxide, in the presence of a catalyst and a hindered amine base in a liquid medium comprising water and a tertiary alcohol.

10 Claims, No Drawings

PROCESS FOR PREPARING 3-ISOCHROMANONE

This invention relates to a chemical process and more particularly to a process for preparing 3-isochromanone which is useful in the manufacture of certain agricultural products.

3-Isochromanone is a well known compound and a number of methods for its preparation are described in the chemical literature. In particular, a process is described in WO97/00850 which comprises reacting an o-xylene-α,α'-dihalide derivative with carbon monoxide and water in an organic solvent in the presence of a catalyst and a hydrogen halide capturing agent followed by treatment with an acid. In this process the hydrogen halide capturing agent is preferably an inorganic base. The use of amines in palladium-catalyzed carbonylation reactions are discussed in J. Org. Chem. [1993] 58, 1538–45 and in U.S. Pat. No. 4,713,484. These references relate, however, to the alkoxycarbonylation of allylphosphates and acetates and to the preparation of carboxylic acid salts.

Thus, according to the present invention, there is provided an improved process for the preparation of 3-isochromanone which comprises contacting an o-xylene-α,α'-dihalide with carbon monoxide in the presence of a catalyst and a hindered amine base in a liquid medium comprising water and a tertiary alcohol.

The o-xylene-α,α'-dihalide starting material has the general formula (I):

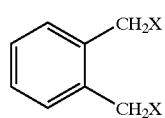
(I)

where X is a halogen atom such as chlorine, bromine or iodine, especially chlorine or bromine. o-Xylene-α,α'-dichloride is a particularly convenient starting material.

The process of the invention is carried out in a liquid medium comprising water and a tertiary alcohol. Suitable tertiary alcohols are monohydric, dihydric or polyhydric alcohols of formula (II):

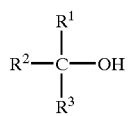
(II)

in which $R^1$, $R^2$ and $R^3$ are independently $C_{1-8}$ alkyl (suitably $C_{1-6}$ alkyl and typically $C_{1-4}$ alkyl), one or more of $R^1$, $R^2$ and $R^3$ being optionally substituted with a phenyl ring or a hydroxyl group, the hydroxyl group being attached to a carbon atom which is itself directly attached to three other carbon atoms.

Of particular interest are aliphatic monohydric and dihydric tertiary alcohols of formula (II) in which $R^1$, $R^2$ and $R^3$ are independently $C_{1-4}$ alkyl, where $C_{1-4}$ alkyl includes methyl, ethyl, n- and iso-propyl and n-, iso-, sec- and tert-butyl, one of $R^1$, $R^2$ and $R^3$ being optionally substituted with a hydroxyl group attached to a carbon atom which is itself directly attached to three other carbon atoms. Examples are 2-methyl propan-2-ol (tert-butanol), 2-methyl butan-2-ol (tert-amyl alcohol), 2,3-dimethylbutan-2-ol, 2-methyl pentan-2-ol, 2-methylhexan-2-ol and 3-methylhexan-3-ol, 2,3-dimethylbutane-2,3-diol (pinacol) and 2,4-dimethylpentane-2,4-diol. Of most interest are monohydric alcohols of formula (II) in which $R^1$, $R^2$ and $R^3$ are independently $C_{1-4}$ alkyl. Tert-Butanol and tert-amyl alcohol are preferred, if only for their commercial availability.

The liquid medium will usually comprise two phases, at least for part of the reaction, depending on the water solubility of the tertiary alcohol. When two phases are present, vigourous agitation is desirable.

Suitably the molar ratio of water:tertiary alcohol is in the range of 1:50 to 50:1, preferably 1:1 to 20:1 and typically 1:1 to 10:1, for example about 2:1 to 7:1.

There will usually be a molar excess of water used in relation to the quantity of o-xylene-α,α'-dihalide starting material. Preferably the molar ratio of water:o-xylene-α-α'-dihalide will be in the range of 100:1 to 1:1 typically 50:1 to 4:1, for example about 30:1 to 5:1.

The carbon monoxide will normally be dispersed into the liquid medium either at atmospheric pressure or at pressures up to 100 atmospheres, for example at from 1 to 10 atmospheres. The pressure chosen will depend on the equipment in which the reaction is carried out and the required reaction rates and yield.

Any suitable carbonylation catalyst may be used in the process of the invention, particularly Group VIII (first, second and third triads) metal catalysts, for example palladium, cobalt or iron catalysts. Especially suitable are palladium catalysts, for example palladium (0) and palladium (II) catalysts, which may be water-soluble or water-insoluble, supported on a carrier, such as carbon, silica or calcium carbonate, a polymer or other inert solid, or unsupported. Supported catalysts have the advantage of facilitating catalyst recovery and recycling. Ligands such as triphenylphosphine may be used in conjunction with certain palladium catalysts or it may be beneficial to pre-reduce the catalyst with hydrogen, or another suitable reducing agent.

Suitable water-soluble palladium catalysts in the form of phoshine complexes are described, for example, by J. Kiji et al in Chem. Lett., 957–960 (1988). Suitable water-insoluble palladium complexes include bis(triphenylphosphine) palladium dichloride and tetrakis(triphenylphosphine) palladium (0) which are described by L. Cassar et al in J. Organometallic Chem., 121 (1976), C55–56, in DE-A-2526046 and by X. Huang et al in Chem. & Ind., Sep. 3, 1990, 548. Palladium (II) catalysed carbonylation reactions are also discussed by V. Grushin et al in Organometallics, 12 (5), 1890–1901 (1993). The use of a supported carbonylation catalyst in the form of palladium-black is described by T. Ito et al in Bull. Chem. Soc. Japan, 48 (7), 2091–2094 (1975). The use of soluble triphenylphosphine ligands to activate palladium catalysts is described by D. Bergbreiter et al in J. Mol. Catalysis, 74 (1992), 409–419. Typical examples of suitable catalysts are palladium chloride (as a solid or in solution in hydrochloric acid or as an aqueous sodium chloride solution), dihydrotetrachloropalladium, disodium tetrachloropalladium, tetrakis (triphenylphosphine) palladium (0), dichlorobis (triphenylphosphine) palladium (II), palladium/carbon, palladium on calcium carbonate and palladium on Montmorillonite™. Other suitable catalysts and ligands, including water soluble ones, are described in WO 97/00850. The ligands may be used in amounts up to 1000 mole equivalents of palladium, and suitably in the range of from 1 to 200 mole equivalents of palladium, for example 10 to 30 mole equivalents. The amount of palladium catalyst used may be in the range of 0.000001 to 0.5 mole equivalents of the o-xylene-α,α'-dihalide.

Where a ligand such as triphenylphosphine is used in combination with a palladium catalyst, the ligand may be added with the catalyst to the reaction mixture or a catalyst-ligand mixture may be preformed for use in the reaction. For example, a melt of triphenylphosphine and palladium chloride ($PdCl_2$) or sodium chloropalladite ($Na_2PdCl_4$) may be solidified and ground into a powder for use in the reaction. It has been found that preformed catalyst-ligand mixtures can speed the uptake of carbon monoxide during reaction and may provide yield benefits. Typically the mole ratio of palladium to phosphorous is 1:10 to 1:30, for example 1:11 or 1:22.

The hindered amine base will usually be one which has at least two aliphatic, preferably branched aliphatic, or cycloaliphatic groups or one in which the N atom is in a cycloaliphatic or aromatic ring, substituted in a manner that induces steric crowding around the N atom. Typically it will be of low water solubility and have a $pK_a$ of the conjugate acid of about 10. Thus, it may be a heteroaromatic base such as pyridine or a substituted pyridine, for example 2,6-dimethylpyridine. Or it may be a secondary amine, providing it is sufficiently sterically hindered. An example of a suitable secondary amine is 2,2,6,6-tetramethyl-piperidine. Preferably, however, it is a tertiary amine of formula $R^1R^2R^3N$ wherein $R^1$, $R^2$ and $R^3$ are independently $C_{1-10}$ alkyl (especially $C_{1-6}$ alkyl) $C_{3-6}$ cycloalkyl, aryl (especially phenyl, but also pyridyl) or aryl($C_{1-4}$)alkyl (especially benzyl), or wherein two or three of $R^1$, $R^2$ and $R^3$ join together with the nitrogen atom to which they are attached to form one, two or three, 5-, 6- or 7-membered alicyclic rings optionally fused and optionally containing a second ring nitrogen atom.

Alkyl groups are straight or branched chain and, unless stated otherwise, contain from 1 to 10, especially from 1 to 6, particularly from 1 to 4, carbon atoms. Examples are methyl, ethyl, iso-propyl, n-propyl, n-butyl, sec-butyl and tert-butyl. Cycloalkyl groups comprise 3 to 6 carbon atoms and are optionally substituted by $C_{1-6}$ alkyl. Examples are cyclohexyl, 2-methylcyclohexyl and 2-ethylcyclohexyl.

Suitable tertiary amines of formula $R^1R^2R^3N$ are, for example, N,N-diisopropylethyl-amine (Hünig's base), N,N-dimethylaniline, triethylamine, t-butyldimethylamine, N,N-diisopropylmethylamine, N,N-diisopropylisobutylamine, N,N-diisopropyl-2-ethylbutylamine, tri-n-butylamine, N,N-dicyclohexylmethylamine, N,N-dicyclohexylethylamine, N-tert-butylcyclohexylamine, N,N-dimethylcyclohexylamine, 1,5-diazabicyclo[4.3.0]non-5-ene, 1,4-diazabicyclo[2.2.2]-octane or 2- or 4-dimethylamino-pyridine.

There will usually be a molar excess of hindered amine base used in relation to the quantity of o-xylene-α,α'-dihalide starting material. Preferably the molar ratio of amine:o-xylene-α,α'-dihalide will be in the range of 10:1 to 1:1, typically 5:1 to 2:1, for example 4:1 to 2.5:1. However, it may be possible to reduce the ratio of amine: o-xylene-α,α'-dihalide to below 1:1, even as low as about 1:100, provided that an inorganic base such as an alkali metal hydroxide, for example sodium or potassium hydroxide, is used in addition. The total amount of base should remain at 1, and preferably at 2 or more, moles per mole of o-xylene-α,α'-dihalide.

When the process is carried out in a two-phase system, it may be advantageous to include a phase transfer catalyst. By the term "phase transfer catalyst" is meant a substance which, being at least partly present in or wetted by a first (usually organic) phase, promotes reaction between a reactant in the first phase and a reactant which it transfers to the first phase from a second (usually aqueous but sometimes solid) phase. After reaction, the phase transfer catalyst is released for transferring further reactant. Phase transfer catalysts are reviewed by E. V. Dehmlow in Angewante Chemie (International Edition), 13 (3), 170 (1974). Other reviews are by Jozef Dockx in Synthesis (1973), 441–456 and by C. M. Starks in JACS., (93) 1, Jan. 13, 1971, 195–199.

Suitably the phase transfer catalyst is a quaternary anmmonium or phosphonium salt preferably containing bulky organic groups, usually alkyl or aralkyl groups, to make it soluble in the organic phase. It is preferred that the phase catalyst is a tetraalkyl or aralkyl (eg benzyl) trialkyl ammonium or phosphonium salt in which the total number of carbon atoms attached to each nitrogen or phosphorus atom is at least 4. There is little advantage in the number being above 70. It is especially preferred that the number should be in the range of from 16 to 40.

Examples of quaternary ammonium salts are: tetramethylammonium chloride, cetyltrimethylammonium bromide, dicetyldimethylammonium chloride, octyltributylammonium bromide, trioctylmethylammonium chloride (available as Aliquat™ 336), benzyldimethyllaurylammonium chloride, benzyltriethylammonium chloride, dilauryldimethylammonium chloride, tetrabutylammonium bromide and dieicosyldimethylammonium chloride. Examples of quaternary phosphonium salts are cetyltripropylphosphonium bromide and triphenylethylphosphonium bromide. Other phase transfer catalysts which may be suitable include crown ethers and polyethylene glycol variants. If used, the phase transfer catalyst may be present in an amount ranging from 0.001 to 0.5 mole equivalents of the o-xylene-α,α'-dihalide.

The process may be carried out at any suitable temperature within a range of from 20° C. to 120° C., preferably from 60° C. to 100° C., typically from 70° C. to 90° C. about 70° C.

After reaction is complete, the 3-isochromanone may be extracted by the addition of aqueous base to form a salt of the corresponding hydroxy acid. From the remaining organic phase the tertiary alcohol and amine may be recovered by distillation, the residues providing a source of catalyst for recovery. From the aqueous layer the 3-isochromanone may be regenerated by suitable pH adjustment, e.g. by acidification with, for example, hydrochloric acid, and extracted into a suitable solvent such as xylene. Carrying out the basification with degassed aqueous base under a blanket of an inert gas such as nitrogen or carbon monoxide, may reduce the formation of tarry material. The tertiary alcohol and amine may be recovered for re-use by, for example, distillation from the aqueous base layer before regeneration of the 3-isochromanone. The catalyst may also be recovered for re-use.

The 3-isochromanone may be recovered at the end of reaction by distillation. Thus, in a first method, the reaction mixture is treated with a base such as an alkali metal hydroxide, the aqueous layer separated, the 3-isochromanone regenerated by pH adjustment and extracted into a suitable solvent such as xylene, as described above. The organic extract is then distilled to remove the solvent and to recover the 3-isochromanone. Alternatively, in a second method, the end-of-reaction mixture is acidified to transfer the amine into the aqueous phase. The resulting organic phase containing the 3-isochromanone, the tertiary alcohol and catalyst is then distilled to recover separately the tertiary alcohol and 3-isochromanone. The catalyst may be recovered from the still residues, or it may be possible to precipitate out a salt of the catalyst, for example a palladium salt, during the acidification, and recover it by filtration prior to distillation.

3-Isochromanone is useful, inter alia, as an intermediate in the manufacture of agricultural products, especially fungicides of the strobilurin type, for example those described in EP-A-278595.

The invention is illustrated by the following Examples in which:

| g = grammes | gc = gas chromatography |
|---|---|
| mmol = millimoles | ° C. = degrees centigrade |
| psi = pounds per square inch | JRV = jacketed reaction vessel |

Pressures recorded in 'bar.g' units are gauge measurements, not absolute. Thus, for example, 4 bar.g is equivalent to 5 bar absolute.

EXAMPLE 1 o-Xylene-α,α'-dichloride (7.0 g, 39.9 mmol) N,N-diisopropylethylamine (15.63 g, 119.7 mmol) palladium chloride ($PdCl_2$) catalyst (0.021 g, 0.1197 mmol), water (7.18 g, 399 mmol) and triphenylphosphine (0.47 g, 1.76 mmol) and tert-butanol (11.9 g, 159.6 mmol) were charged to a 100 ml round bottom flask and carbon monoxide bubbled through via a syringe needle. The reaction mixture was heated to 70° C. with fast agitation while bubbling carbon monoxide through. A sample tested by qualitative gc analysis after 3 hours showed the reaction to be complete.

Sodium hydroxide (6.38 g at 100% strength) and water (16.5 g) were added to the reaction mixture, which was then stirred at 60° C. for 1 hour before separating an organic layer A (26.66 g) and an aqueous layer. Concentrated hydrochloric acid (12.31 g at 35.5% strength) and o-xylene (21 g) were added to the aqueous layer, which was stirred at 60° C. for 1 hour before separating a xylene solution B (26.94 g) and an aqueous layer C (40.35 g). Quantitative gc analysis showed 3-isochromanone present as follows:

Organic layer A 0.04% (0.18% yield)
Xylene solution B 15.01% (68.48% yield)
Aqueous layer C 0.2% (1.4% yield)
Total yield of 3-isochromanone 70.06%

EXAMPLE 2

Palladium chloride (0.043 g, 0.24 mmol), triphenyl phosphine (0.93 g, 4 mmol), N,N-diisopropylethylamine (31 g, 240 mmol), water (14.4 g, 800 mmol), o-xylene-α,α' dichloride (14 g, 80 mmol) and tert-amyl alcohol (33.8 g, 384 mmol) were charged to a 310 ml PARR reactor, fitted with an agitator and carbon monoxide charging system. The stirrer was switched on after the temperature was adjusted to 70° C. and the pressure increased to 4 bar.g (60 psig). The vessel pressure was maintained at 60 psig using carbon monoxide and the temperature between 70–75° C. by heating/cooling. When the carbon monoxide uptake ceased, the pressure was released back to atmosphere and the 3-isochromanone product was extracted from the organic phase using aqueous sodium hydroxide (12.8 g at 100% strength, 320 mmol). The 3-isochromanone was regenerated by addition of hydrochloric acid (7.3 g at 35.5% strength, 200 mmol) and extracted into o-xylene (42.5 g, 400 mmol). The resultant solution was analysed for 3-isochromanone and found to contain 16.8% w/w. This represents a yield of 75.4% of 3-isochromanone from xylene-αα' dichloride.

EXAMPLE 3 o-Xylene-α,α'-dichloride (14.7 g at 95% strength, 80 mmol), N,N-diisopropylethylamine (31.4 g at 99% strength, 250 mmol), an aqueous solution of dihydrotetrachloropalladium ($H_2PdCl_4$) catalyst (0.1271 g at 53.8% strength, 0.27 mmol), tert-amyl alcohol (28.2 g at 95% strength, 300 mmol), water (14.4 g, 800 mmol) and triphenylphosphine (0.93 g at 99% strength, 3.5 mmol) were charged to a 300 ml Inconel™ autoclave. The autoclave was purged three times at 5 bar.g with carbon monoxide gas before being finally pressurised to about 4 bar.g. The reaction mixture was briskly agitated (~900 rpm) and heated to 70° C. Once at temperature, the reaction mixture was stirred at 70° C. for approximately 4 hours, the pressure being maintained at about 4 bar.g and the rate of uptake of carbon monoxide gas noted. The reaction was adjudged complete when no further carbon monoxide was seen to be consumed. The reaction mixture was then rapidly cooled to below 40° C. and sampled to test for the presence of starting material by gc. Water (33 g) and sodium hydroxide (27.4 g at 47% strength) were charged in one portion to the open autoclave, which was then sealed and purged with carbon monoxide gas three times at 5 bar.g before finally being pressurised to 1 bar.g. The reaction mixture was then stirred at 60° C. under 1–2 bar.g (CO pressure) for approximately 1 hour. The two phases were then transferred to a hot separator (in air) and separated at 60° C., the aqueous phase being drawn off for further work-up.

The aqueous phase was added cautiously to a stored solution of o-xylene (41.4 g) and concentrated hydrochloric acid (19.8 g at 36% strength) at 60° C. (in air). The mixture was then stirred for 1 hour at 60° C. before being separated to give an aqueous waste stream and a xylene solution containing the product, 3-isochromanone; yield 83.7%.

A repeat experiment gave a yield of 83.9%.

EXAMPLE 4 o-Xylene-α,α'-dichloride (14.7 g at 95% strength, 80 mmol), N,N-diisopropyl-ethylamine (25.5 g at 99% strength, 200 mmol), an aqueous solution of dihydrotetrachloropalladium ($H_2PdCl_4$) catalyst (0.0586 g at 53.8% strength, 0.126 mmol), tert-amyl alcohol (14.1 g, 163 mmol,) water (28.8 g, 1600 mmol) and triphenylphosphine (2.1 g at 95% strength, 8.0 mmol) were charged to 300 ml Inconol™ autoclave. The autoclave was purged three times at 5 bar.g with carbon monoxide gas before finally being pressurised to about 4 bar.g. The reaction mixture was briskly agitated (~900 rpm) and heated to 70° C. Once at temperature, the reaction mixture was stirred at 70° C. for approximately 4 hours, the pressure being maintained at about 4 bar.g and the rate of uptake of carbon monoxide gas noted. The reaction was adjudged complete when no further carbon monoxide was seen to be consumed. The reaction mixture was then rapidly cooled to below 40° C. and sampled to test for the presence of starting material by gc. Water (33 g) and sodium hydroxide (27.4 g at 47% strength) were charged in one portion to the open autoclave, which was then sealed and purged with carbon monoxide gas three times at 5 bar.g before finally being pressurised to 1 bar.g The reaction mixture was then stirred at 60° C. under 1–2 bar.g (CO pressure) for approximately 1 hour. The two phases were then transferred to a hot separator (in air) and separated at 60° C., the aqueous phase being drawn off for further work-up.

The aqueous phase was added cautiously to a stirred solution of o-xylene (41.4 g) and concentrated hydrochloric acid (19.8 g at 36% strength) at 60° C. (in air). The mixture was then stirred for 1 hour at 60° C. before being separated to give an aqueous waste stream and a xylene solution containing the product, 3-isochromanone; yield 75.8%.

EXAMPLE 5 o-Xylene-α,α'-dichloride (14.7 g at 95% strength, 80 mmol), N,N-diisopropyl-ethylamine (29.24 g at 99% strength, 224 mmol), an aqueous solution of dihydrotetrachloropalladium ($H_2PdCl_4$) catalyst (0.075 g at 53.8% strength, 0.16 mmol), tert-amyl alcohol (21.37 g at 99% strength, 240 mmol), water (25.2 g, 1400 mmol) and triphenylphosphine (2.11 g at 99% strength, 8 mmol) were charged to a 310 ml PARR autoclave fitted with an agitator and carbon monoxide charging system. The autoclave was pressurised to 60 psi with carbon monoxide and this pressure was maintained throughout the reaction, which was carried out at 70° C. The reaction was adjudged complete when no further carbon monoxide was seen to be consumed.

The contents of the autoclave were transferred to a beaker where a sample of the reaction mixture was withdrawn. The autoclave was evacuated and the reaction mixture recharged to the autoclave by vacuum displacement. Sodium hydroxide solution was prepared in the same beaker with pearl sodium hydroxide (12.8 g at 100% strength) and water (22.32 g). This was also transferred to the autoclave by vacuum displacement. The mixture was now stirred at 60° C. for 1 hour at 15 psi before transferring the contents to a separating funnel. The two phases were separated to give an aqueous layer, which was carried forward to the acid work up, and an organic layer of 46.99 g. The aqueous layer was added to a stirred mixture of xylene (42.46 g) at 60° C. and concentrated hydrochloric acid (20.56 g at 35.5% strength) This mixture was stirred at 60° C. for one hour before being separated to give an aqueous layer (77.56 g) and a xylene solution (53.25 g). Quantitive analysis showed 46.99 g 3-isochromanone at 0.03% (0.12% yield) in the organic layer, 77.56 g 3-isochromanone at 0.19% (0.25% yield) in the aqueous layer and 53.25 g 3-isochromanone at 18.04% (81.13% yield) in the xylene solution: total chemical yield 82.5%.

EXAMPLE 6 o-Xylene-α,α'-dichloride (14.7 g at 95% strength, 80 mmol), N,N-diisopropyl-ethylamine (31.4 g at 99% strength, 240 mmol, nitrogen degassed), tert-amyl alcohol (33.8 g at 100% strength, 384 mmol, nitrogen degassed), palladium chloride ($PdCl_2$) catalyst (0.043 g at 99% strength, 0.24 mmol), triphenylphosphine (2.12 g at 99% strength, 8 mmol) and water (14.4 g, 800 mmol, nitrogen degassed), were charged to a 310 Inconel™ autoclave. The autoclave was purged three times at 5 bar.g with carbon monoxide (technical grade), before being finally pressurised to 4 bar.g. The reaction liquors were agitated at 1000 rm and heated to 70° C. The reaction temperature was maintained at 70° C. for approximately 4 hours maintaining the carbon monoxide pressure at approximately 4 bar.g throughout the reaction period, noting the rate of uptake of carbon monoxide. Reaction was deemed to be complete when no further carbon monoxide was seen to be consumed. A stirred sample of reaction liquors was removed from the autoclave and tested by gc for the presence of o-xylene-α,α'-dichloride.

The autoclave was cooled to 60° C., agitation was stopped and the autoclave vented to approximately 1 bar.g. This residual pressure was used to discharge the reaction liquors (clear, amber, single phase) to a jacketed reaction vessel (JRV), which had been previously brought to 60° C. and purged with nitrogen. A positive flow of nitrogen was maintained throughout the workup in the JRV to eliminate oxygen incursion. Aqueous sodium hydroxide (60.9 g at 21% strength, nitrogen degassed) was added to the stirred reaction liquors via a balanced dropping funnel which had been purged with nitrogen. The resulting liquors were stirred for approximately 1 hour then allowed to settle enabling a phase separation to take place. This consisted of an upper clear red organic phase, a lower clear red aqueous base phase and a slight black dispersion located at the interface. The lower aqueous base phase was weighed off and stored for workup later. The black dispersion was seen to adhere to the walls of the JRV on discharge of the lower phase. Air was then blown over the stirred upper organic phase allowing air incursion. Within 1 to 2 minutes severe tarring of the organic phase was seen confirming that oxygen exclusion was in fact needed during workup to avoid tarring. The organic phase was then discharged. The aqueous base phase was reintroduced in air to a clean JRV which had been heated to 60° C. and agitated at 400 rpm.

o-Xylene (42.5 g at 100% strength, 400 mmol) was introduced to the JRV followed by cautious addition of hydrochloric acid (20.3 g at 36% strength, 0.2 mmol), Fuming was evident and the liquors were allowed to stir for approximately 1 hour. The liquors were then allowed to stand at 60° C. enabling two phases to be separated. The lower clear acidic aqueous phase was weighed off, followed by the upper clear red/amber o-xylene solution of 3-isochromanone (approximately 18% w/w). The previously recovered organic phase, acidic aqueous phase and o-xylene solution were analysed by gc for 3-isochromanone; yield: organic phase 0.37%, acidic aqueous phase 1.56%, o-xylene solution 73.9%: total 75.8%.

EXAMPLE 7 o-Xylene-α,α'-dichloride (7.35 g at 95% strength, 40 mmol), N,N-diisopropyl-ethyllamine (15.7 g at 99% strength, 120 mmol), an aqueous solution of dihydrotetrachloropalladium ($H_2PdCl_4$) catalyst (0.0651 g at 53.8% strength, 0.14 mmol), tert-amyl alcohol (14.1 g at 95% strength, 150 mmol), water (14.4 g, 800 mmol) and triphenylphosphine (1.1 g at 99% strength, 4 mmol) were charged to a 100 ml round bottom flask. The vessel was sealed and vacuum purged with carbon monoxide gas three times. The contents of the reaction vessel were briskly agitated (~900 rpm) and heated to 70° C., with a steady bubbling of carbon monoxide through the mixture. Once at temperature, the reaction mixture was stirred at 70° C. for approximately 2.25 hours, maintaining the steady bubbling. The reaction mixture was sampled to test for the presence of starting material by gc.

Sodium hydroxide solution (30.2 g at 21% strength) was charged in one portion to the flask, which was sealed. Carbon monoxide was then bubbled through the mixture again. The reaction mixture was stirred at 60° C., with steady bubbling for approximately 1 hour. The two phases were transferred to a hot separator (in air) and separated at 60° C., the aqueous phase being drawn off for fisher workup. The organic phase was retained for a recycle reaction (see Recycle 1).

The aqueous phase was added cautiously to a stirred solution of xylene (20.7 g) and concentrated hydrochloric acid (9.9 g at 36% strength) at 60° C. (in air). The mixture was stirred for 1 hour at 60° C. before separating to give an aqueous waste stream and a xylene solution containing the product, 3-isochromanone.

Recycle 1

The organic phase obtained above was charged to a 100 ml round bottom flask. The same amounts of o-xylene-α,α'-dichloride, triphenylphosphine, water and palladate catalyst as above were charged to the same flask. The vessel was sealed and vacuum purged with carbon monoxide gas three times. The contents of the reaction vessel were briskly agitated (~900 rpm) and heated to 70° C., with a steady bubbling of carbon monoxide through the mixture. Once at temperature, the reaction mixture was stirred at 70° C. for approximately 2 hours, maintaining the steady bubbling. The reaction mixture was sampled to test for the presence of starting material by gc.

Sodium hydroxide solution (30.2 g at 21% strength) was charged in one portion to the flask, which was sealed. Carbon monoxide gas was bubbled through the mixture again. The reaction mixture was stirred at 60° C., with steady bubbling for approximately 1 hour. The two phases were transferred to a hot separator (in air) and separated at 60° C., the aqueous phase being drawn off for farther work-up. The organic phase was retained for a recycle reaction (see Recycle 2).

The aqueous phase was added cautiously to a stirred solution of xylene (20.7 g) and concentrated hydrochloric acid (9.9 g at 36% strength) at 60° C. (in air). The mixture was stirred for 1 hour at 60° C. before separating to give an aqueous waste stream and a xylene solution containing the product, 3-isochromanone.

Recycle 2

The organic phase obtained from Recycle 1 was charged to a 100 ml round bottom flask. The same amounts of o-xylene-α,α'-dichloride, triphenylphosphine, and water as above were charged to the same flask. The vessel was sealed and vacuum purged with carbon monoxide gas three times. The contents of the reaction vessel were briskly agitated (~900 rpm) and heated to 70° C., with a steady bubbling of carbon monoxide through the mixture. Once at temperature, the reaction mixture was stirred at 70° C. for approximately 2 hours, maintaining the steady bubbling. The reaction mixture was sampled to test for the presence of starting material by gc.

Sodium hydroxide solution was charged in one portion to the flask, which was sealed. Carbon monoxide gas was bubbled through the mixture again. The reaction mixture was stirred at 60° C., with steady bubbling for approximately 1 hour. The two phases were transferred to a hot separator and separated at 60° C., the aqueous phase being drawn off for further work-up (Note: tarring observed at this point).

The aqueous phase was added cautiously to a stirred solution of xylene (20.7 g) and concentrated hydrochloric acid (9.9 g at 36% strength) at 60° C. (in air). The mixture was stirred for 1 hour at 60° C. before separating to give an aqueous waste stream and a xylene solution containing the product, 3-isochromanone.

Yields: Initial experiment 82.3%; Recycle 1 69.9%; Recycle 2 73.7%.

EXAMPLE 8 o-Xylene-α,α'-dichloride (14.24 g at 98.3% strength, 80 mmol) N,N-diisopropyl-ethylamine (31.33 g at 99% strength, 240 mmol), t-amyl alcohol (21.37 at 99% strength, 240 mmol), water (28.8 g, 1600 mmol) and catalyst mixture preformed as described below (1.065 g to give 3.52 mmol triphenylphosphine and 0.16 mmol catalyst) were charged to a 310 ml Hastelloy™ autoclave. The autoclave was purged three times with carbon monoxide (premium grade) at 75 psi before being finally pressurised to 30 psi. The reaction liquors were agitated at 1000 rpm whilst heating to 70° C. The reaction temperature was held at 70° C., maintaining the pressure at 30 psi throughout the reaction period. Reaction was deemed to be complete when carbon monoxide uptake ceased. The vessel was vented to ~15 psi and the mixture heated to 100° C. to facilitate the precipitation of palladium. The reaction was stirred at 500 rpm at 100° C. for one hour before transferring to a nitrogen-blanketed JRV. Aqueous sodium hydroxide (60.59 g at 21% strength) was added to the JRV and stirred at 60° C. for one hour, maintaining the nitrogen blanket. Separation was carried out to give a lower aqueous layer which was retained for further work-up and an upper organic layer (48.32 g). The aqueous layer was recharged to the vessel along with xylene (42.46 g) and concentrated hydrochloric acid (20.56 g at 35.5% strength). This mixture was stirred at 60° C. for one hour before separating to give a lower aqueous layer (97.0 g; 3-isochromanone strength 0.22%; 1.8% yield) and an upper xylene solution of 3-isochromanone. (52.59 g; 3-isochromanone strength 17.84%; 79.15% yield). Total chemical yield by quantative gc analysis, 80.95%.

Preparation of Preformed Catalyst Mixture

Triphenylphosphine (10.1010 g, 38.1 mmol) was charged to a 3-necked 100 ml round bottom flask and heated to 90° C. with rapid agitation to produce a melt. Sodium chloropalladite ($Na_2PdCl_4$) solution (1.4594 g, 1.732 mmol) was added dropwise to the melt and the reaction mixture was agitated until the catalyst mixture was produced as a yellow slurry. The mixture was allowed to cool and the catalyst solidified. The solid was removed from the flask and powdered using a mortar and pestle. This catalyst was used directly in the above carbonylation reaction. Assuming a quantitative chemical yield of 100%, the catalyst had a palladium strength of 1.60% w/w (with a palladium to phosphorous mole ratio of 1:22).

EXAMPLE 9

A reactor vessel was purged and vented four times using nitrogen at a pressure of 1 barG. To the reactor vessel was charged tertiary-amyl alcohol (48 kg, 0.55 kg mol), de-ionised water (92 kg, 5 kg mol) o-xylene-α,α'-dichloride (45 kg, 0.25 kg mol), tertiary-amyl alcohol (10 kg, 0.11 kg mol) as a line wash for residual o-xylene-α,α'-dichloride and the palladium chloride-triphenylphosphine catalyst species formed prior to addition using the following method.

Preparation of Catalyst

Triphenylphosphine (1.50 kg, 0.0057 kg mol) was charged to a 2-liter reaction vessel and heated to 90° C. with rapid agitation to produce a melt. Palladium chloride in hydrochloric acid solution (0.125 kg, 0.00025 kg mol) was added dropwise to the melt and the reaction mixture was agitated until the catalyst was produced as a yellow slurry. The 2-liter reaction vessel was removed from the source of heat and the yellow slurry poured into a pyrex dish. The catalyst readily solidified and was subsequently broken up using a mortar and pestle for use as a powder in the reaction. The above process was repeated for a second charge of triphenylphosphine (1.5 kg, 0.0057 kg mol), and assuming a quantitative chemical yield of 100% the catalyst had a palladium strength of 1.66%.

The reactor vessel was purged and vented four times using nitrogen at a pressure of 1 barG. To the reactor vessel was charged N,N-diisopropylethylamine (99 kg, 0.75 kg mol) and tertiary-amyl alcohol (10 kg, 0.11 kg mol) as a line wash for residual N,N-diisopropylethylamine. The reactor vessel was purged and vented four times using nitrogen at a pressure of 1 barG, followed by being purged and vented twice using carbon monoxide at a pressure of 4 barG. The reactor vessel was heated to 40° C. at a pressure of 3–3.5 barG under carbon monoxide. The exotherm from the reaction raised the batch temperature to 70° C. The batch was then controlled at 70° C. to within ±5° C. using pressurised hot water until the carbon monoxide uptake ceased (ca 10 kg). The pressure of the reactor vessel was reduced by venting the carbon monoxide to the atmosphere, and the temperature of the reactor vessel was reduced to 40° C. The reactor vessel was purged and vented four times using nitrogen at a pressure of 1 barG. The contents of the reactor vessel were analysed for the end of reaction by gc.

The reactor vessel was purged and vented twice using carbon monoxide at a pressure of 4 barG and left at a pressure of 1 barG using carbon monoxide. The reactor vessel was heated to 100° C. and held at this temperature for 1 hour, and the pressure of the reactor vessel was reduced by venting the carbon monoxide to the atmosphere. The reactor vessel was cooled to 55–60° C. and purged and vented four times using nitrogen at a pressure of 1 barG. To the reactor vessel was charged de-ionised water (108 kg, 6 kg mol) and 47% sodium hydroxide (87 kg, 1.025 kg mol). The reactor vessel was held at 55–60° C. for 30 minutes and the contents then allowed to settle for 1 hour after stirring was stopped. The lower aqueous phase was separated and filtered via a Pall screening cartridge, and after stirring was started the organic phase was discharged to an earthed drum.

The aqueous phase distilled under a vacuum of 50 mmHg at a temperature of 55° C. until a change in distillate appearance was apparent. The distillate was then discharged to an earthed drum. To the remaining aqueous phase was charged o-xylene (130 kg, 1.28 kg mol) and hydrochloric acid (65 kg, 0.64 kg mol) maintaining the reactor vessel at a temperature of 55–60° C. throughout the course of the addition. The reactor vessel was stirred for 1 hour at 55–60° C. and then analysed for pH (<2). The contents were then allowed to settle for 1 hour after stirring was stopped, and the aqueous and o-xylene phases were separated to individual earthed drums. The solution of 3-isochromanone in o-xylene (166.5 kg) was analysed as 18.37% w/w/strength (30.59 kg at 100% weight). This represents an isolated yield of 82.58%. The chemical yield for the process was analysed to be 84.53%.

What is claimed is:

1. A process for the preparation of 3-isochromanone which comprises contacting an o-xylene-α,α'-dihalide with carbon monoxide, in the presence of a palladium catalyst and N,N-diisopropylethylamine in a liquid medium comprising water and a tertiary alcohol, the molar ratio of N,N-diisopropylethylamine:o-xylene-α,α'-dihalide being in the range of 10:1 to 1:1 and the molar ratio of water:tertiary alcohol being in the range of 1:1 to 20:1.

2. A process according to claim 1 in which the o-xylene-α,α'-dihalide is o-xylene-α,α'-dichloride.

3. A process according to claim 1 in which in the tertiary alcohol is an alcohol of formula (II):

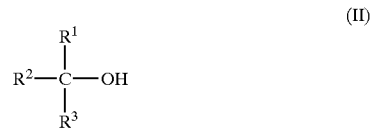

in which $R^1$, $R^2$ and $R^3$ are independently $C_{1-8}$ alkyl, one or more of $R^1$, $R^2$ and $R^3$ being optionally substituted with a phenyl ring or a hydroxyl group, the hydroxyl is group being attached to a carbon atom which is itself directly attached to three other carbon atoms.

4. A process according to claim 3 in which the tertiary alcohol is tert-amyl alcohol or tert-butanol.

5. A process according to claim 3 in which the molar ratio of water:o-xylene-α,α'-dihalide is in the range of 100:1 to 1:1.

6. A process according to claim 1 in which the palladium catalyst is present in the amount of 0.000001 to 0.5 mole equivalents of the o-xylene-α,α'-dihalide.

7. A process according to claim 1 in which a triphenylphosphine ligand is used in combination with the palladium catalyst in the range of from 1 to 200 mole equivalents of phosphorous to palladium.

8. A process according to claim 7 in which the triphenylphosphine ligand and palladium catalyst are used in a preformed mixture.

9. A process according to claim 3 in which there is present a phase transfer catalyst.

10. A process according to claim 3 which is carried out at a temperature of from 20° C. to 200° C.

* * * * *